(12) United States Patent
Yasuhira et al.

(10) Patent No.: US 7,631,476 B2
(45) Date of Patent: Dec. 15, 2009

(54) STEAM-REPLACEMENT DEAERATION APPARATUS FOR USE IN BAG PACKAGING

(75) Inventors: Masanori Yasuhira, Iwakuni (JP);
Kiyokazu Mizote, Iwakuni (JP);
Masanao Hashimoto, Iwakuni (JP)

(73) Assignee: Toyo Jidoki Co., Ltd., Tokyo (JP)

( * ) Notice: Subject to any disclaimer, the term of this patent is extended or adjusted under 35 U.S.C. 154(b) by 0 days.

(21) Appl. No.: 11/999,410

(22) Filed: Dec. 5, 2007

(65) Prior Publication Data
US 2008/0134630 A1  Jun. 12, 2008

(30) Foreign Application Priority Data
Dec. 12, 2006  (JP) .............................. 2006-334029
Oct. 25, 2007  (JP) .............................. 2007-277707

(51) Int. Cl.
*B65B 31/06* (2006.01)
(52) U.S. Cl. ........................ 53/434; 53/111 R; 53/79; 53/407
(58) Field of Classification Search ............... 53/111 R, 53/79, 407, 425, 432, 433, 434, 510–512; 426/232, 461, 476, 486, 488; 422/26, 28, 422/108
See application file for complete search history.

(56) References Cited

U.S. PATENT DOCUMENTS

| 4,081,942 A | 4/1978 | Johnson |
| 4,173,215 A * | 11/1979 | Bureau et al. ............... 126/369 |
| 4,318,431 A * | 3/1982 | Evans ........................... 141/90 |
| 4,418,512 A * | 12/1983 | Johnson ....................... 53/434 |
| 4,418,513 A * | 12/1983 | Plahm .......................... 53/434 |
| 4,830,278 A * | 5/1989 | Kohmura et al. .............. 99/468 |
| 5,271,893 A * | 12/1993 | Newman ...................... 422/26 |
| 6,199,601 B1 | 3/2001 | Laudenberg |
| 6,622,462 B2 * | 9/2003 | Wakabayashi et al. ........ 53/510 |
| 2001/0026826 A1 * | 10/2001 | Tottenham et al. .......... 426/521 |
| 2002/0159915 A1 | 10/2002 | Zelina et al. |
| 2006/0000242 A1 * | 1/2006 | Yang et al. .................... 68/5 R |

FOREIGN PATENT DOCUMENTS

| EP | 0 418 079 A1 | 3/1991 |
| EP | 0 440 042 A2 | 8/1991 |
| JP | HEI-7-86012 B | 9/1995 |

\* cited by examiner

*Primary Examiner*—Hemant M Desai
(74) *Attorney, Agent, or Firm*—Daniel P. Burke & Associates, PLLC

(57) ABSTRACT

Steam from a steam supply source is heated in a heating device, supplied to a nozzle through a secondary steam supply passage and injected from a spout. The temperature of steam at the outlet of the heating device is measured by a first sensor, and a cartridge heater constituting the heating device is controlled on the basis of the difference between the measured temperature and a target value. Steam temperature at the nozzle spout is measured by a second sensor, and a difference between the measured temperature and a target value is obtained. The target value of steam temperature at the heating device outlet is changed to a set value predetermined according to the magnitude of the difference obtained.

36 Claims, 11 Drawing Sheets

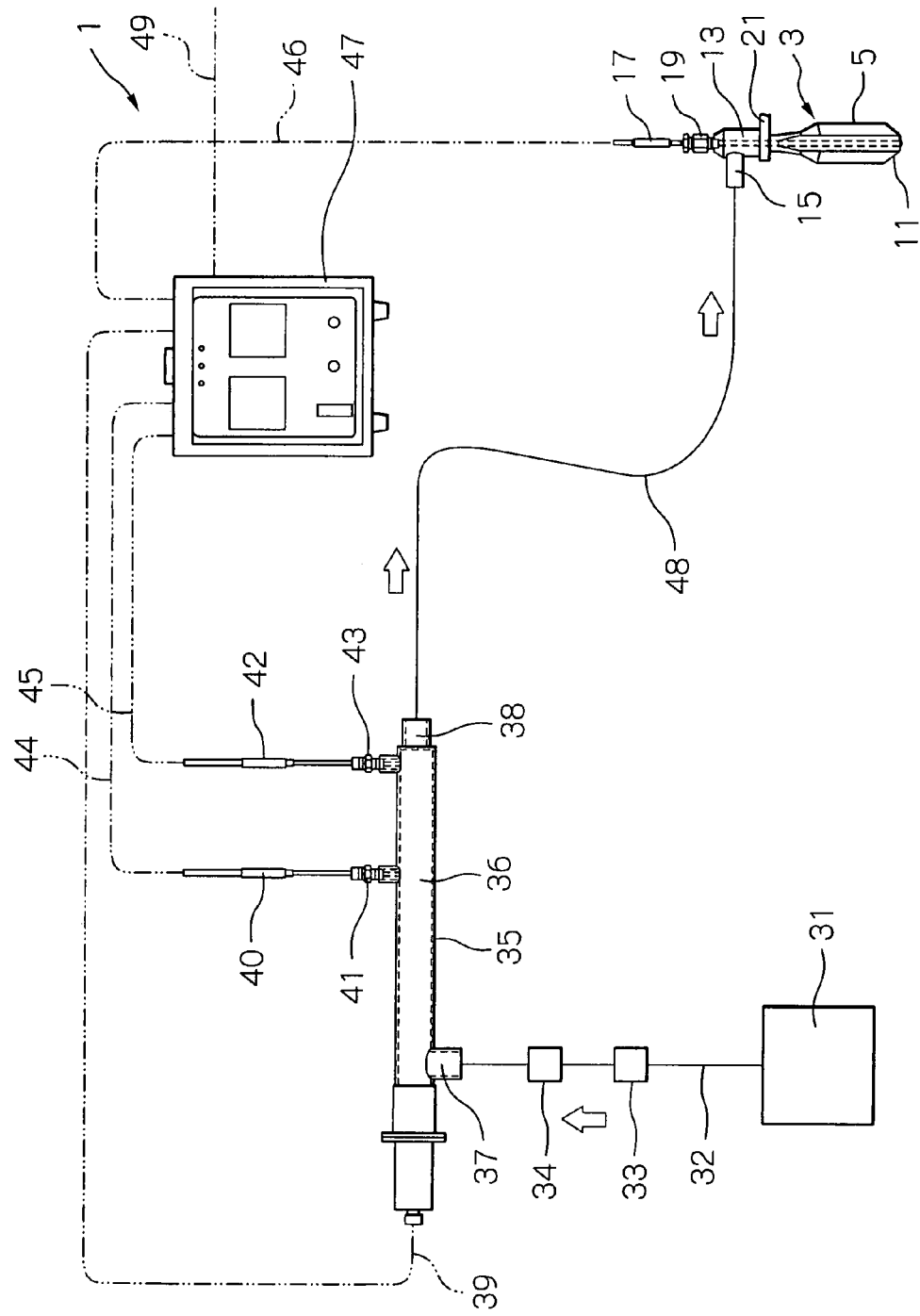

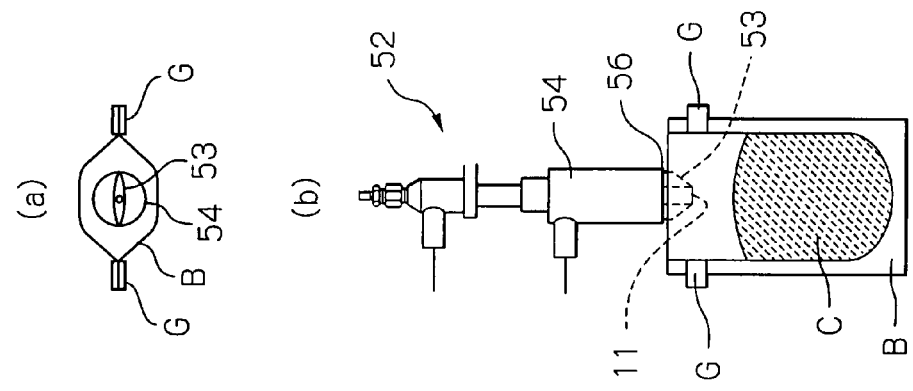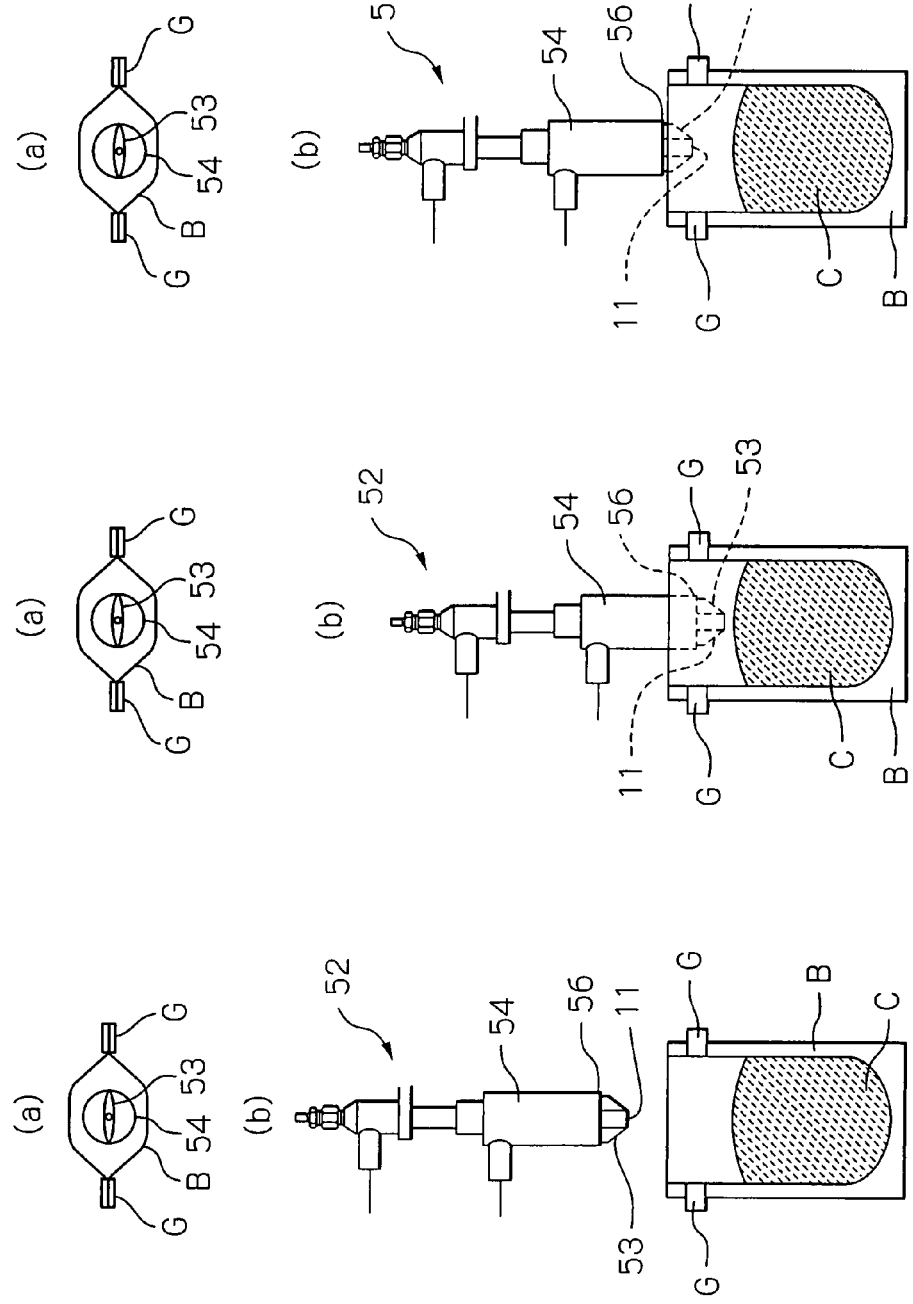

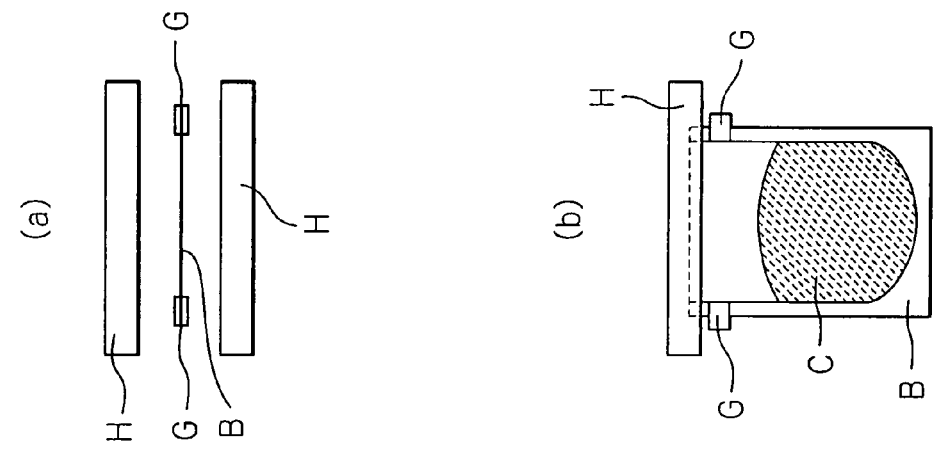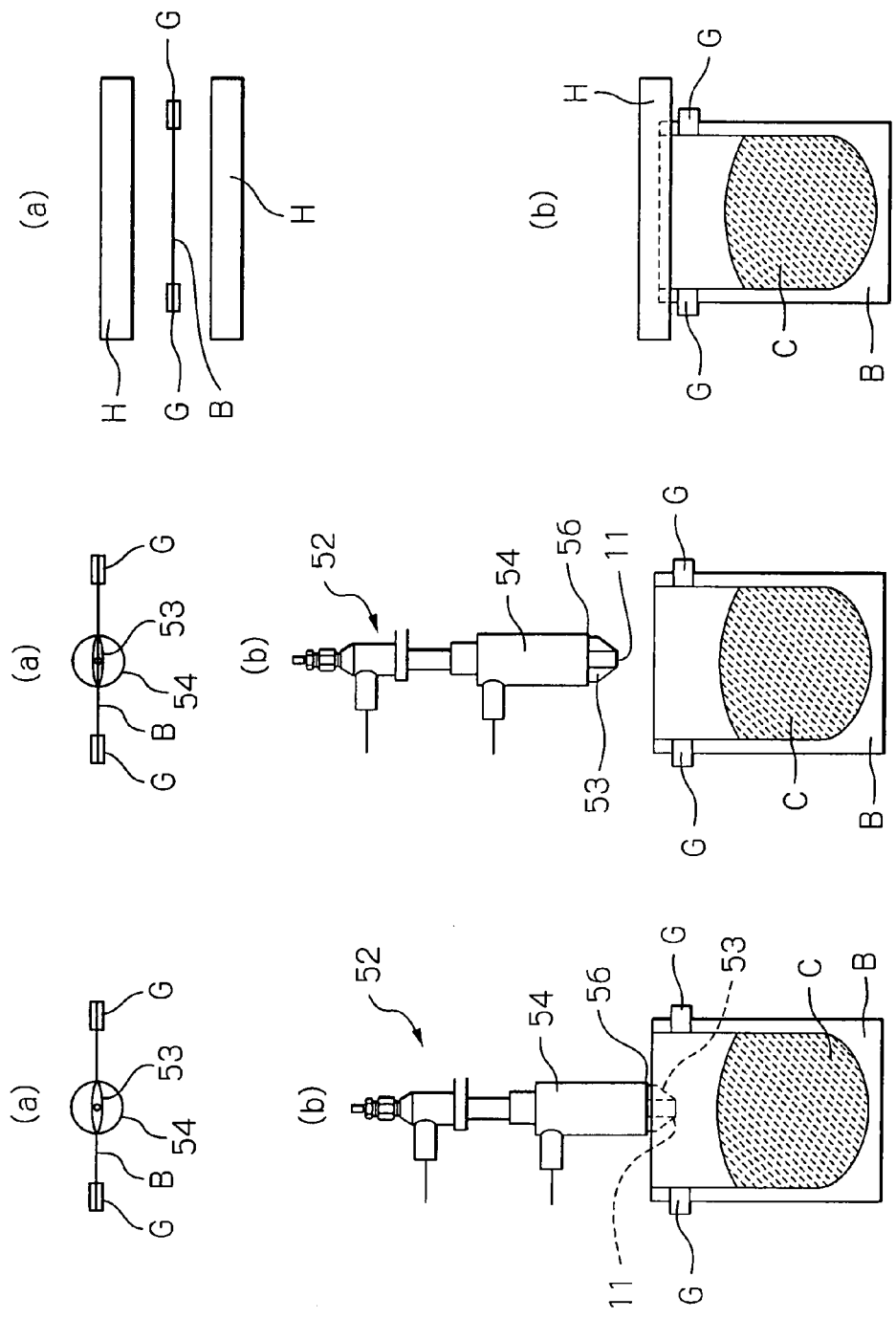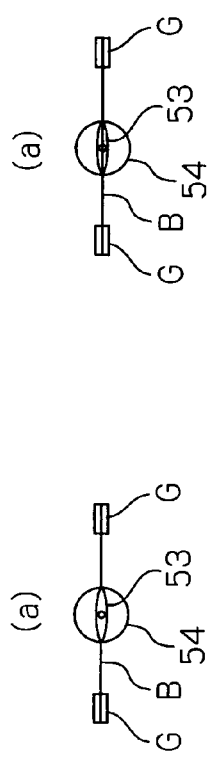

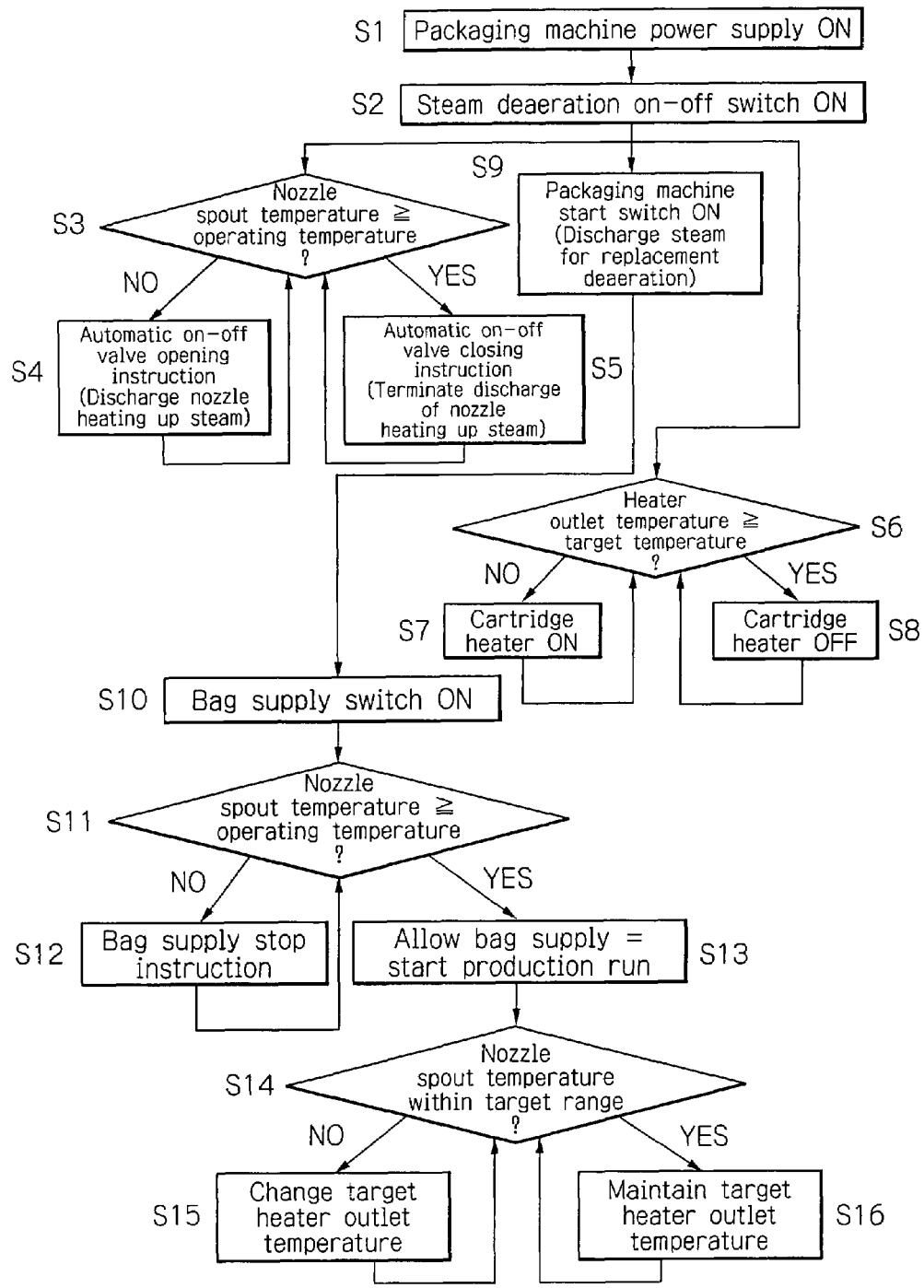

STEAM-REPLACEMENT DEAERATION APPARATUS FOR USE IN BAG PACKAGING

BACKGROUND OF THE INVENTION

1. Field of the Invention

The present invention relates to a steam-replacement deaeration apparatus and method for use in bag packaging. More particularly, the present invention relates to a steam-replacement deaeration apparatus and method capable of appropriately controlling the temperature of steam to be injected. The present invention further relates to a steam-replacement deaeration apparatus and method capable of appropriately controlling the steam temperature and also capable of rapidly heating up steam injected from a nozzle to an appropriate temperature for steam-replacement deaeration, thereby reducing the standby time of a bag packaging operation.

2. Discussion of Related Art

In automatic bag packaging of food products or the like, steam-replacement deaeration is performed in which steam is blown into a bag after it has been filled with an article to be packaged to replace the air in the bag with the steam, thereby effecting deaeration. The temperature of steam injected into the bag is important because it influences the contraction of the internal volume of the bag after cooling and also a treatment carried out after the deaeration, e.g. a sterilization treatment.

Conventional steam-replacement deaeration apparatus used in bag packaging are generally arranged as follows. Steam supplied from a steam supply source is heated in a heating device incorporating a cartridge heater, and the heated steam is sent to a nozzle through a steam supply passage. The steam temperature at the outlet of the heating device is measured, and a signal representing the outlet steam temperature is feedbacked to control ON/OFF of the heater so that the outlet steam temperature reaches a target value. The surface temperature of the heating device is also measured to prevent the heater from overheating when no steam is flowing therethrough, thereby preventing a failure of the heating device.

In the conventional steam-replacement deaeration apparatus, steam from the heating device is sent to the nozzle through the steam supply passage. Therefore, a temperature drop naturally occurs during the delivery of the steam. Consequently, the temperature of steam actually injected from the nozzle differs from the steam temperature at the outlet of the heating device. Further, even if the temperature at the heating device outlet is the same, the temperature drop differs according to the change of the ambient temperature, or between when the apparatus has started its operation and when it is in steady-state operation, resulting in a difference in the temperature of steam injected from the nozzle. For this reason, deaeration failure occurs frequently, and the operator needs to make an adjustment every time such failure occurs.

Japanese Patent Application Post-Exam Publication No. Hei 7-86012 discloses an arrangement for controlling a heater in automatic packaging using cup-shaped semirigid containers in which steam and an inert gas are successively blown into each container. In the disclosed arrangement, a coil heater is wound around a steam pipe, through which steam passes, as far as near the end of a steam branch pipe, and a heat-insulating material is wound on the coil heater. Steam passing through the steam pipe is heated by the coil heater, and the temperature of steam is measured with a thermometer attached sidewardly to a lower end outlet of the steam branch pipe from which steam is injected. A signal representing the measured temperature is sent to a controller to control the heater. In this regard, bag packaging process using bag-shaped containers needs to insert the steam injection nozzle into a bag in order to obtain a satisfactory deaerated state and therefore cannot employ an arrangement as disclosed in the above-mentioned patent document, wherein a pipe through which steam passes is per se wound with a coil heater and a heat-insulating material to heat steam passing therethrough, and a thermometer is attached sidewardly to a lower end outlet of the pipe.

SUMMARY OF THE INVENTION

The present invention has been made in view of the above-described problems associated with the related art.

Accordingly, an object of the present invention is to provide a steam-replacement deaeration apparatus and method capable of eliminating the influence of changes in the temperature of steam during moving through the steam supply passage and also capable of rapidly controlling the temperature of steam injected from the nozzle to a predetermined target temperature even if there are differences in conditions between when the apparatus has started its operation and when it is in steady-state operation or even if the ambient temperature or other environmental conditions change, thereby stably obtaining a deaerated state at a high replacement rate.

Another object of the present invention is to provide a steam-replacement deaeration apparatus and method capable of raising the temperature of steam injected from the nozzle to a predetermined operating temperature stably in a reduced period of time by supplying steam to the nozzle prior to starting a bag packaging operation under conditions different from those for injection during the bag packaging operation.

To eliminate the influence of changes in the temperature of steam during moving through the steam supply passage, the present invention provides a steam-replacement deaeration apparatus for use in a bag packaging machine. The apparatus includes a nozzle having at a distal end thereof a spout to be inserted into a packaging bag, a steam supply source for supplying steam to the nozzle, and a heating device that heats steam to be supplied to the nozzle. The apparatus further includes a primary steam supply passage connected at opposite ends thereof to the steam supply source and the heating device, respectively, and a secondary steam supply passage connected at opposite ends thereof to the heating device and the nozzle, respectively. A first temperature sensor is disposed near an outlet for steam of the heating device to measure the temperature of steam at the outlet, and a second temperature sensor is disposed in the nozzle to measure the temperature of steam in a neighborhood of the spout of the nozzle. The apparatus further includes a controller that controls the heating device on the basis of a first target temperature set as a target temperature of steam at the outlet of the heating device and a signal from the first temperature sensor, and changes and resets the first target temperature on the basis of a second target temperature set as a target temperature of steam at the spout of the nozzle and a signal from the second temperature sensor.

To rapidly raise the steam temperature at the spout of the nozzle to a predetermined operating temperature to thereby reduce the standby time of the packaging machine, the steam-replacement deaeration apparatus of the present invention is further provided with a heat-up steam supply passage for continuously supplying steam to the nozzle to heat it prior to starting the supply of the bag performed by a bag supply device. The supply of steam through the heat-up steam supply passage is controlled by the controller.

The present invention is also applied to a steam-replacement deaeration apparatus for use in a bag packaging machine that uses a double-tube type nozzle having two nozzle members, i.e. inner and outer nozzle members. In this apparatus, to eliminate the influence of changes in the temperature of steam during moving through the steam supply passage, the two nozzle members are respectively provided with heating devices, primary steam supply passages, secondary steam supply passages, and pairs of first and second temperature sensors. The controller controls the two heating devices and changes and resets the first target temperatures for the heating devices.

To rapidly raise the steam temperature at the spout of each nozzle member to a predetermined operating temperature to thereby reduce the standby time of the packaging machine, the steam-replacement deaeration apparatus using a double-tube type nozzle further includes a heat-up steam supply passage provided for at least the outer nozzle member to continuously supply steam to the nozzle member to heat it prior to the start of supply of the bag performed by a bag supply device. The supply of steam through the heat-up steam supply passage is controlled by the controller.

In addition, the present invention provides a steam-replacement deaeration method for use in bag packaging that is capable of eliminating the influence of changes in the temperature of steam during moving through the steam supply passage. The method uses a nozzle having at a distal end thereof a spout to be inserted into a bag. The nozzle is connected to a steam supply source through a steam supply passage. The method further uses a heating device disposed in the steam supply passage to heat steam passing therethrough. According to the method, a first target temperature is set as a target temperature of steam at an outlet of the heating device. A second target temperature is set as a target temperature of steam at the spout of the nozzle. An actual heater outlet steam temperature at the outlet of the heating device is measured. An actual nozzle spout steam temperature in a neighborhood of the spout of the nozzle is measured. The heating device is controlled on the basis of the first target temperature and the actual heater outlet steam temperature measured. The first target temperature is changed and reset on the basis of the second target temperature and the actual nozzle spout steam temperature measured.

To rapidly raise the steam temperature at the spout of the nozzle to a predetermined operating temperature to thereby reduce the standby time of the packaging machine, the method of the present invention further includes the step of continuously supplying steam to the nozzle prior to starting a bag packaging operation to raise the temperature of the nozzle to the operating temperature. More specifically, the continuous supply of steam to the nozzle is performed through a heat-up steam supply passage provided between the heating device and the steam supply source that supplies steam to the heating device in parallel to the steam supply passage.

According to the present invention, the set value of a target temperature of steam at the outlet of the heating device, i.e. first target temperature, is changed by using the difference between the temperature of steam at the nozzle spout detected by the second temperature sensor, i.e. actual nozzle spout steam temperature, and a target temperature of steam at the nozzle spout, i.e. second target temperature. Therefore, it is possible to eliminate the influence of changes in the temperature of steam during moving through the steam supply passage. In addition, the actual nozzle spout steam temperature can be appropriately and rapidly controlled to the target nozzle spout steam temperature even if the actual nozzle spout steam temperature at the start of production changes or the actual nozzle spout steam temperature fluctuates due to environmental condition changes. Accordingly, the occurrence of deaeration failure can be minimized.

In addition, a heat-up steam supply passage is provided, and steam for heating up is continuously supplied to the nozzle through the heat-up steam supply passage prior to starting a bag packaging operation, specifically, starting the supply of the bag performed by a bag supply device. By doing so, the nozzle can be heated to a predetermined operating temperature stably and rapidly. Thus, the standby time needed until the start of a bag packaging operation can be reduced.

Other objects and advantages of the present invention will become apparent from the following detailed description of illustrated embodiments of the invention.

BRIEF DESCRIPTION OF THE DRAWINGS

FIG. 2 is a circuit diagram showing the arrangement of a steam-replacement deaeration apparatus according to a first embodiment of the present invention.

FIGS. 6A to 6F are diagrams showing the procedure of steam-replacement deaeration in the second embodiment.

FIG. 10 is a flowchart showing the operation of the steam-replacement deaeration apparatus according to the fourth embodiment.

DETAILED DESCRIPTION OF THE PREFERRED EMBODIMENTS

Embodiments of the present invention will be described below with reference to the accompanying drawings. It should be noted that the following embodiments are for illustrative purposes only, and that the scope of the present invention is not limited to these embodiments.

Figure 1:
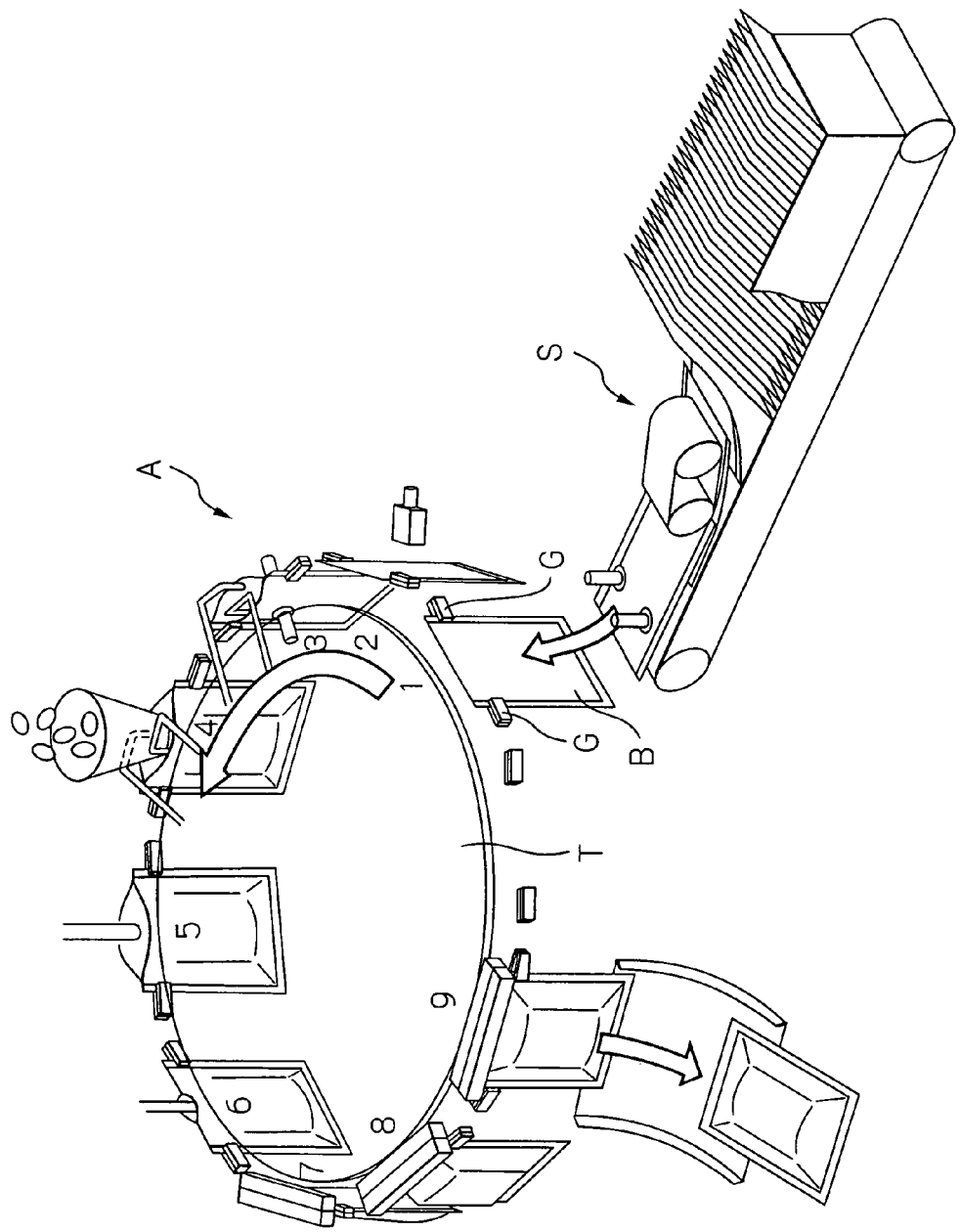
FIG. 1 is a perspective view schematically showing a bag packaging machine using a steam-replacement deaeration apparatus according to the present invention.

FIG. 1 is a perspective view schematically showing a bag packaging machine A using a steam-replacement deaeration apparatus (hereinafter referred to simply as "deaeration apparatus") 1 according to the present invention. The packaging machine A has a turntable T equipped with a plurality of pairs of grippers G. At step 1, a bag B supplied from a bag supply device S is gripped with a pair of grippers G. In this state, the bag B is moved through various steps successively. At step 2, the bag B is printed with data such as the date of manufacture.

At step 3, the mouth of the bag B is opened. At step 4, a solid material is filled into the bag B. At step 5, a liquid material is filled into the bag B. At step 6, the air in the bag B is replaced with steam by a deaeration apparatus 1 (described later). Thus, the bag B is deaerated. At step 7, the mouth of the bag B is subjected to first sealing process. At step 8, the bag mouth is subjected to second sealing process. At step 9, the bag mouth is cooled, and the bag B is discharged as a product.

Figure 3A:
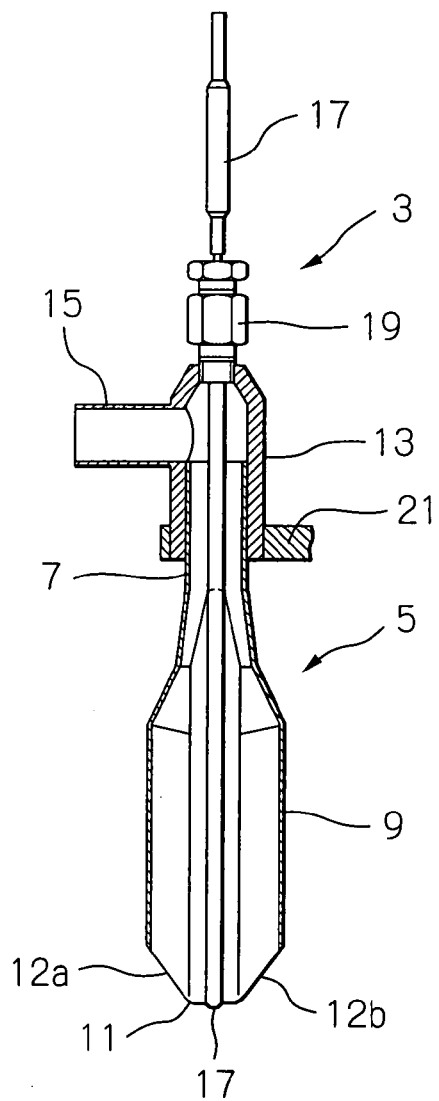
FIGS. 3A and 3B are a sectional side view and a bottom view, respectively, showing a nozzle used in the first embodiment.
Figure 3B:
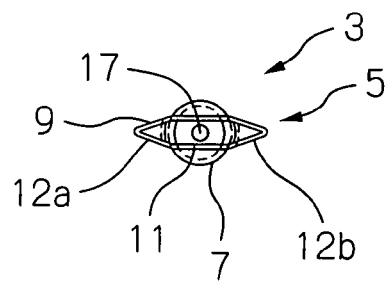

FIG. 2 is a circuit diagram showing the arrangement of a deaeration apparatus 1 according to a first embodiment of the present invention. FIGS. 3A and 3B show a nozzle 3 used in the first embodiment. First, the arrangement of the nozzle 3 will be explained with reference to FIGS. 3A and 3B.

FIG. 3A is a sectional side view of the nozzle 3. FIG. 3B is a bottom view of the nozzle 3, in which illustration of some constituent members is omitted. The nozzle 3 has a nozzle body 5 extending vertically in FIG. 3A. The nozzle body 5 has a substantially cylindrical upper tubular part 7 and an insert part 9 below the upper tubular part 7. At least a lower end portion of the insert part 9 is adapted to be inserted into a packaging bag (not shown). As will be clear from FIG. 3B, the insert part 9 has a flat cross-sectional configuration. The nozzle 3 has a spout 11 at the lower end, i.e. distal end, of the insert part 9. The spout 11 has been obliquely cut at longitudinally opposite ends thereof to form slant portions 12a and 12b. The cross-sectional configuration of the insert part 9 is not necessarily limited to that shown in FIG. 3B but may be any flat shape.

The upper end of the nozzle body 5 is secured to a hollow holder 13. The holder 13 has a steam inlet 15 provided on a side thereof. The steam inlet 15 is connected to a secondary steam supply passage 48 (see FIG. 2), which will be described later. The holder 13 has a hole formed in the upper end thereof. A temperature sensor 17 is fitted into the hole by using an adapter 19. The temperature sensor 17 extends downward through the nozzle body 5 as far as the spout 11 to detect the temperature of steam injected from the spout 11. The nozzle 3 is fixedly secured to an elevating shaft (not shown) through a mounting bracket 21 so as to move up and down together with the elevating shaft. Thus, the spout 11 is inserted into a bag (not shown) to inject steam thereinto. Upon completion of the injecting operation, the spout 11 is removed from the bag. The operation of inserting the spout 11 into the bag and removing it therefrom is publicly known. Therefore, a description thereof is omitted herein.

Next, the first embodiment of the present invention will be explained with reference to FIG. 2. Reference numeral 31 in the figure denotes a steam supply source, which may be of the same type as conventionally used. The steam supply source 31 is connected to an inlet 37 of a heating device 35, which may also be of the same type as conventionally used, through a primary steam supply passage 32. The primary steam supply passage 32 is provided at its intermediate portion with a pressure-reducing valve 33 and a flow passage on-off valve 34. The heating device 35 incorporates a publicly known cartridge heater 36 therein. The heater 36 is connected to a controller 47 (described later) through wiring 39, so that the ON/OFF of the heater 36 is properly controlled by the controller 47. Reference numeral 38 denotes an outlet of the heating device 35, i.e. a steam outlet.

A temperature sensor 40 is attached to the heating device 35 by using an adapter 41 to measure the surface temperature of the cartridge heater 36. A temperature sensor (first temperature sensor) 42 is attached near the outlet 38 of the heating device 35 by using an adapter 43 to measure the temperature of steam flowing out of the outlet 38. The sensors 40 and 42 are connected to the controller 47 through respective wiring 44 and 45. The above-described temperature sensor 17 (second temperature sensor), which is attached to the nozzle 3, is also connected to the controller 47 through wiring 46. The above-described turntable T and bag supply device S (see FIG. 1) are also connected to the controller 47 through wiring 49, so that the operations of these devices are controlled by the controller 47. The outlet 38 of the heating device 35 is connected to the steam inlet 15 of the nozzle 3 by the secondary steam supply passage 48.

The following is an explanation of the operation of the steam-replacement deaeration apparatus 1 having the above-described structure. First, a packaging bag (not shown) is filled with an article to be packaged at the preceding step, and sent to the deaeration step in a state where the laterally opposite side edges thereof are gripped by a pair of grippers and the bag mouth is open. When the bag has moved to directly below the nozzle 3 that is in a standby position, the nozzle 3 starts to move downward. During the downward movement of the nozzle 3, more specifically, substantially at the same time as the spout 11 of the nozzle 3 enters the bag, the on-off valve 34 is opened. Consequently, steam from the steam supply source 31 is sent to the heating device 35 through the primary steam supply passage 32 after the pressure thereof has been properly reduced by the pressure-reducing valve 33. The steam is heated in the heating device 35. The heated steam comes out of the outlet 38, passes through the secondary steam supply passage 48 and enters the nozzle 3 through the steam inlet 15. Thus, the injection of steam from the spout 11 into the bag is started. The injection of steam is continued as it is. When the nozzle 3 reaches the extremity of its downward movement, it remains in this position for a short period of time. During this time, the grippers gripping the laterally opposite side edges of the bag are moved away from each other by a predetermined distance, whereby the bag mouth is tensed to come in close contact with the nozzle 3. Thereafter, the nozzle 3 starts to move upward. During the upward movement of the nozzle 3, more specifically, substantially at the same time as the spout 11 of the nozzle 3 comes out of the bag, the on-off valve 34 is closed to stop the injection of steam. The nozzle 3 returns to a predetermined standby position. Meanwhile, the bag is sent to the subsequent step with the bag mouth kept in the tensed state. It should be noted that the steam injection start and stop timings can be properly changed. When steam is injected from the nozzle 3, the sensor 42 measures the temperature of steam at the outlet 38 of the heating device 35, and the sensor 17 measures the temperature of steam at the spout 11 of the nozzle 3. The sensors 42 and 17 send respective signals to the controller 47. It should be noted that when the power supply of the controller 47 is on, the surface temperature of the heater 36 is constantly measured by the temperature sensor 40 to prevent the heater 36 from overheating.

Next, steam temperature control will be explained. First, a target nozzle spout steam temperature (second target temperature), which is a target value of the temperature of steam injected from the nozzle 3, is input to the controller 47. Also set and input to the controller 47 is an initial value of a target heater outlet steam temperature (first target temperature), which is a target temperature of the steam temperature at the heater outlet 38 that is determined allowing for a temperature drop in the secondary steam supply passage 48. The controller 47 is supplied with an input signal representing the actual temperature of steam at the heater outlet 38, which is detected by the sensor 42, i.e. actual heater outlet steam temperature. The controller 47 compares the actual heater outlet steam temperature with the set target heater outlet steam temperature and performs control on the basis of the comparison result so that the actual heater outlet steam temperature reaches the target heater outlet steam temperature by properly turning on/off the cartridge heater 36. Meanwhile, the controller 47 is supplied with an input signal representing the actual temperature of steam at the spout 11 of the nozzle 3, which is detected by the sensor 17, i.e. actual nozzle spout steam temperature. The controller 47 compares the actual nozzle spout steam temperature with the set target nozzle spout steam temperature and changes, on the basis of the magnitude of the difference therebetween, the preset value of the target heater outlet steam temperature to a set value predetermined in correspondence with the magnitude of each difference between actual and target nozzle spout steam temperatures. Thereafter, the above-described control of the heater outlet steam temperature by the use of the signal from the sensor 42 is performed by using the newly set target heater outlet steam temperature as a target value. This operation is repeated to control the actual nozzle spout steam temperature to the target nozzle spout steam temperature.

It should be noted that the controller 47 is also connected to the turntable T and the bag supply device S through the wiring 49, as has been stated above. The controller 47 controls the system so that the packaging machine A is kept idling in standby mode, for example, by stopping the supply of bags B by the bag supply device S until the temperature of steam detected by the second temperature sensor 17 reaches a predetermined operating temperature, even if the switch of the packaging machine A is turned on. The packaging operation is started when the steam temperature has reached the operating temperature. When the temperature detected by the second temperature sensor 17 becomes lower than the operating temperature after the start of the operation, bags treated at that temperature are disposed of as defective products.

Unlike the above, if the actual temperature at the spout 11 of the nozzle 3 is feedbacked to control the operation of the heater 36 by using the difference between the actual temperature and the target temperature to thereby directly control the temperature at the spout 11, for example, the deviation of the actual temperature from the target temperature is large due to the influence of the temperature drop in the steam supply passage 48, so that it takes a time to make the actual temperature approach the target value. There are cases where the actual temperature does not converge to the target value but diverges, resulting in the control itself becoming impossible. In contrast, the present invention enables the actual temperature to be controlled to the target value surely in a reduced period of time because the controller 47 obtains a difference of the actual nozzle spout steam temperature at the spout 11 of the nozzle 3 from the target nozzle spout steam temperature and resets the set value of the target heater outlet steam temperature to a newly set value corresponding to the magnitude of the difference obtained.

Figure 4:
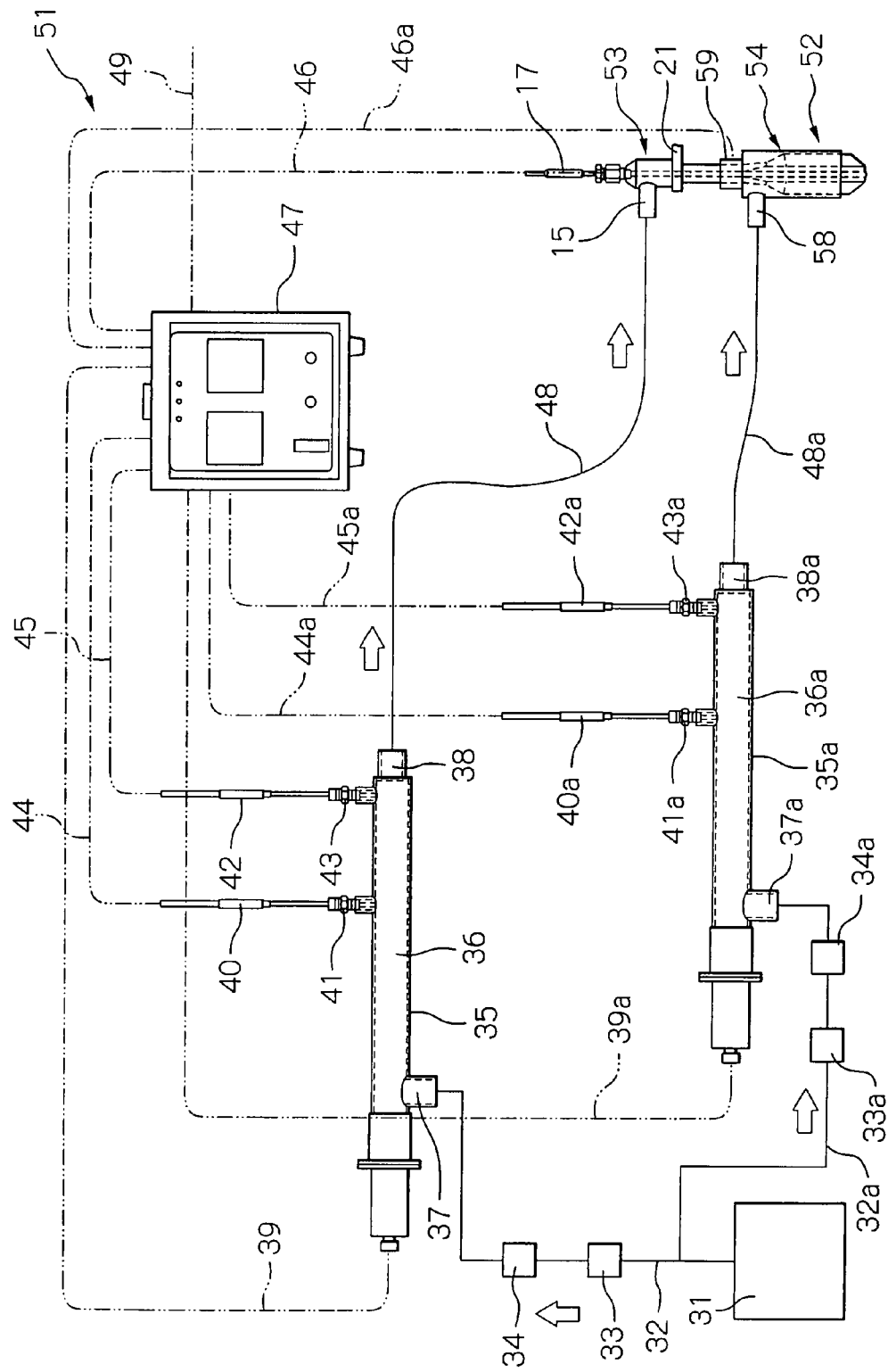
FIG. 4 is a circuit diagram showing the arrangement of a steam-replacement deaeration apparatus according to a second embodiment of the present invention.
Figure 5A:
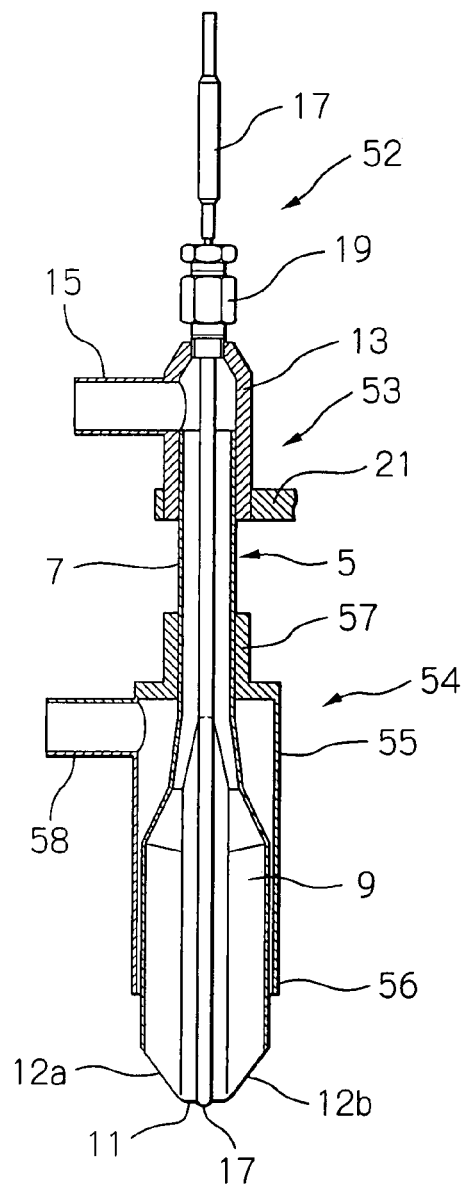
FIGS. 5A and 5B are a sectional side view and a bottom view, respectively, showing a nozzle used in the second embodiment.
Figure 5B:
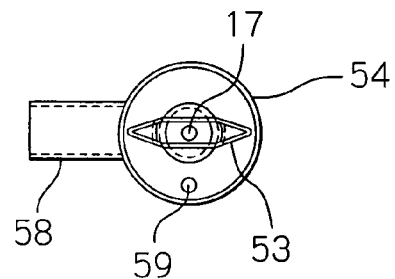

Next, a deaeration apparatus 51 according to a second embodiment of the present invention will be explained with reference to FIGS. 4 to 6F. First, a nozzle 52 used in this embodiment will be explained with reference to FIGS. 5A and 5B. FIG. 5A is a sectional side view of the nozzle 52. FIG. 5B is a bottom view of the nozzle 52, in which illustration of some constituent members is omitted. The nozzle 52 has a double-tube structure formed from an inner first nozzle member 53 and an outer second nozzle member 54. The first nozzle member 53 differs from the nozzle 3 used in the first embodiment only in the length of the upper tubular part 7 of the nozzle body 5. The arrangement of the rest of the first nozzle member 53 is the same as that of the nozzle 3. Therefore, the corresponding members are denoted by the same reference numerals as used in the first embodiment, and a detailed description thereof is omitted herein.

The outer second nozzle member 54 is a substantially cylindrical member and has a cylindrical nozzle body 55 with a spout 56 at the lower end, i.e. distal end, thereof. The nozzle body 55 surrounds a lower portion of the upper tubular part 7 and the insert part 9 of the first nozzle member 53. The second nozzle member 54 is secured to the upper tubular part 7 of the first nozzle member 53 at a mounting portion 57 formed on the upper side of the nozzle body 55. The second nozzle member 54 moves up and down together with the first nozzle member 53 as one unit so that the spouts 11 and 56 of the first and second nozzle members 53 and 54 are inserted into the bag. The nozzle body 55 has a steam inlet 58 provided in an upper side portion thereof. As will be clear from FIG. 5A, the lower end of the spout 56 of the second nozzle member 54 is axially rearward of the lower end of the spout 11 of the first nozzle member 53. That is, the lower end of the spout 56 is located above the lower end of the spout 11 as viewed in FIG. 5A. A temperature sensor 59 is disposed in the second nozzle member 54 so that the distal end thereof is positioned near the distal end of the spout 56 of the second nozzle member 54.

Next, the deaeration apparatus 51 according to the second embodiment will be explained with reference to FIG. 4. As will be clear from the foregoing description of the nozzle 52 and also from FIG. 4, the apparatus 51 is constructed by adding members necessary for controlling the temperature of steam injected from the second nozzle member 54 of the nozzle 52 to the arrangement of the first embodiment shown in FIG. 2. The same arrangement as that shown in FIG. 2 is used as it is for the control of the temperature of steam injected from the first nozzle member 53. Therefore, in FIG. 4 the same members as those shown in FIG. 2 are denoted by the same reference numerals as used in the first embodiment, and a detailed description thereof is omitted herein. That is, reference numerals are used to denote as follows: 31 is a steam supply source; 32 is a primary steam supply passage; 33 is a pressure-reducing valve; 34 is a flow passage on-off valve; 35 is a heating device; 36 is a cartridge heater; 37 is an inlet; 38 is an outlet; 39 is wiring; 40 and 42 are temperature sensors; 41 and 43 are adapters; 44, 45 and 46 are wiring; 47 is a controller; 48 is a secondary steam supply passage; and 49 is wiring.

The steam supply source 31 and the controller 47 are used in common for the first and second nozzle members 53 and 54. Other members provided for the second nozzle member 54 are similar to those provided for the first nozzle member 53. Therefore, the members for the second nozzle member 54 are denoted by using the same reference numerals as those of the corresponding members for the first nozzle member 53, with the letter "a" suffixed thereto.

The steam supply source 31 is also connected to an inlet 37*a* of a second heating device 35*a* through a steam supply passage 32*a* branched from the steam supply passage 32. The steam supply passage 32*a* is also provided at its intermediate portion with a pressure-reducing valve 33*a* and a flow passage on-off valve 34*a*. The heating device 35*a* incorporates a cartridge heater 36*a* therein. The heater 36*a* is connected to the controller 47 through wiring 39*a*, so that the ON/OFF of the heater 36*a* is properly controlled by the controller 47. Reference numeral 38*a* denotes an outlet of the heating device 35*a*, i.e. a steam outlet.

A temperature sensor 40*a* is attached to the heating device 35*a* by using an adapter 41*a* to measure the surface temperature of the cartridge heater 36*a*. A temperature sensor 42*a* is attached near the outlet 38*a* of the heating device 35*a* by using an adapter 43*a* to measure the temperature of steam flowing out of the outlet 38*a*. The sensors 40*a* and 42*a* are connected to the controller 47 through respective wiring 44*a* and 45*a*.

The above-described temperature sensor 59, which is attached to the second nozzle member 54, is also connected to the controller 47 through wiring 46a. Further, the bag packaging machine (not shown) is also connected to the controller 47 through wiring 49, so that the operation of the machine is controlled by the controller 47, as in the case of the first embodiment. The outlet 38a of the heating device 35a is connected to the steam inlet 58 of the second nozzle member 54 by a steam supply passage 48a.

Next, the procedure of steam-replacement deaeration using the nozzle 52 will be explained with reference to FIGS. 6A to 6F. FIG. 6A shows a state where a bag B filled with an article C to be packaged has moved to and stopped at the deaeration step. The bag B has been sent to the deaeration step in a state where the laterally opposite side edges thereof are gripped by a pair of grippers G and the bag mouth has been kept open from the preceding step. The nozzle 52 is standing by directly above the bag B moved there. In each of FIGS. 6A to 6F, part (a) is a plan view, and part (b) is a side view.

FIG. 6B shows a state where the nozzle 52 has moved downward from the position shown in FIG. 6A until the spouts 11 and 56 of the first and second nozzle members 53 and 54 are inserted into the bag B as far as respective predetermined positions, and steam is being injected from the spouts 11 and 56. It should be noted that the injection of steam may be started at any of the following timings: the same time as the downward movement of the nozzle 52 is started; when the nozzle 52 has lowered to a predetermined position; and when both the spouts 11 and 56 have completely entered the bag B. In the illustrated state, steam is injected into the bag B from the first and second nozzle members 53 and 54 for a predetermined period of time.

FIG. 6C shows a state where after steam has been injected from the first and second nozzle members 53 and 54 for a predetermined period of time, the nozzle 52 has been moved upward by a predetermined distance to an intermediate position to remove only the second nozzle member 54 from the bag B, and where the steam injection from the second nozzle member 54 has been stopped. In this state, the spout 11 of the first nozzle member 53 is located in the bag B, and the steam injection therefrom is continuing. At this time, because the distal end portion of the spout 11 of the first nozzle member 53 has been obliquely cut at longitudinally opposite ends thereof to form slant openings, as has been stated above, steam is injected from the spout 11 not only directly downward but also obliquely downward. Accordingly, steam can be injected uniformly throughout the bag B. It should be noted that the injection of steam from the second nozzle member 54 may be stopped at any of the following timings: the same time as the upward movement of the nozzle 52 is started; when the nozzle 52 has moved upward by a predetermined distance; and when the nozzle 52 is stopped at an intermediate position.

In FIG. 6D, the nozzle 52 remains in the position shown in FIG. 6C. That is, the nozzle 52 is at rest at the intermediate position. Steam is being injected from the first nozzle member 53. The injection of steam from the second nozzle member 54 is kept stopped. In this state, the grippers G are moved away from each other by a predetermined distance to bring the bag mouth into a tensed state so that the bag mouth is in close contact with the periphery of the insert part 9 of the first nozzle member 53. In this case, because the insert part 9 has a flat cross-sectional configuration, it is possible to minimize the gap between the insert part 9 of the first nozzle member 53 and the bag mouth. In this state, steam is continuously injected from the first nozzle member 53 for a predetermined period of time.

FIG. 6E shows a state where the nozzle 52 has been moved upward by a predetermined distance from the position shown in FIG. 6D to the standby position shown in FIG. 6A to remove the spout 11 of the first nozzle member 53 from the bag B, and where the injection of steam from the first nozzle member 53 has been stopped. The grippers G remain at the same positions as the above, so that the mouth of the bag B is kept closed in the tensed state. In this state, the bag B is moved to the sealing step shown in FIG. 6F. At the sealing step, the bag mouth is sealed by using a pair of publicly known hot plates H. With the nozzle 52, at the first stage of steam injection, a large amount of steam is injected from both the first and second nozzle members 53 and 54. At the second stage of steam injection, the entry of external air into the bag can be prevented. Thus, deaeration of a high replacement rate can be performed within a reduced period of time.

In the steam-replacement deaeration apparatus 51 arranged as stated above, the first nozzle member 53 and the second nozzle member 54 are controlled independently of each other. In this regard, the control for each of the first and second nozzle members 53 and 54 is the same as stated in the first embodiment. Therefore, a description thereof is omitted herein. It should be noted, however, that the steam injection stop timing differs for the first and second nozzle members 53 and 54, as will be clear from the foregoing description made with reference to FIGS. 6A to 6F. The steam injection stop timings of the first and second nozzle members 53 and 54 are controlled by the on-off valves 34 and 34a, respectively. It is also possible to use the steam supply passages 32 and 48 in common and to control the steam temperature at both the first and second nozzle members 53 and 54 by using only the heating device 35 and the temperature sensors 40 and 42 attached thereto. However, because the first and second nozzle members 53 and 54 differ from each other in the steam injection stop timing, as has been stated above, it is necessary at least to branch the steam supply passage 48 into two passages before it connects with the first and second nozzle members 53 and 54 and to provide respective on-off valves in the two branch passages.

Figure 7:
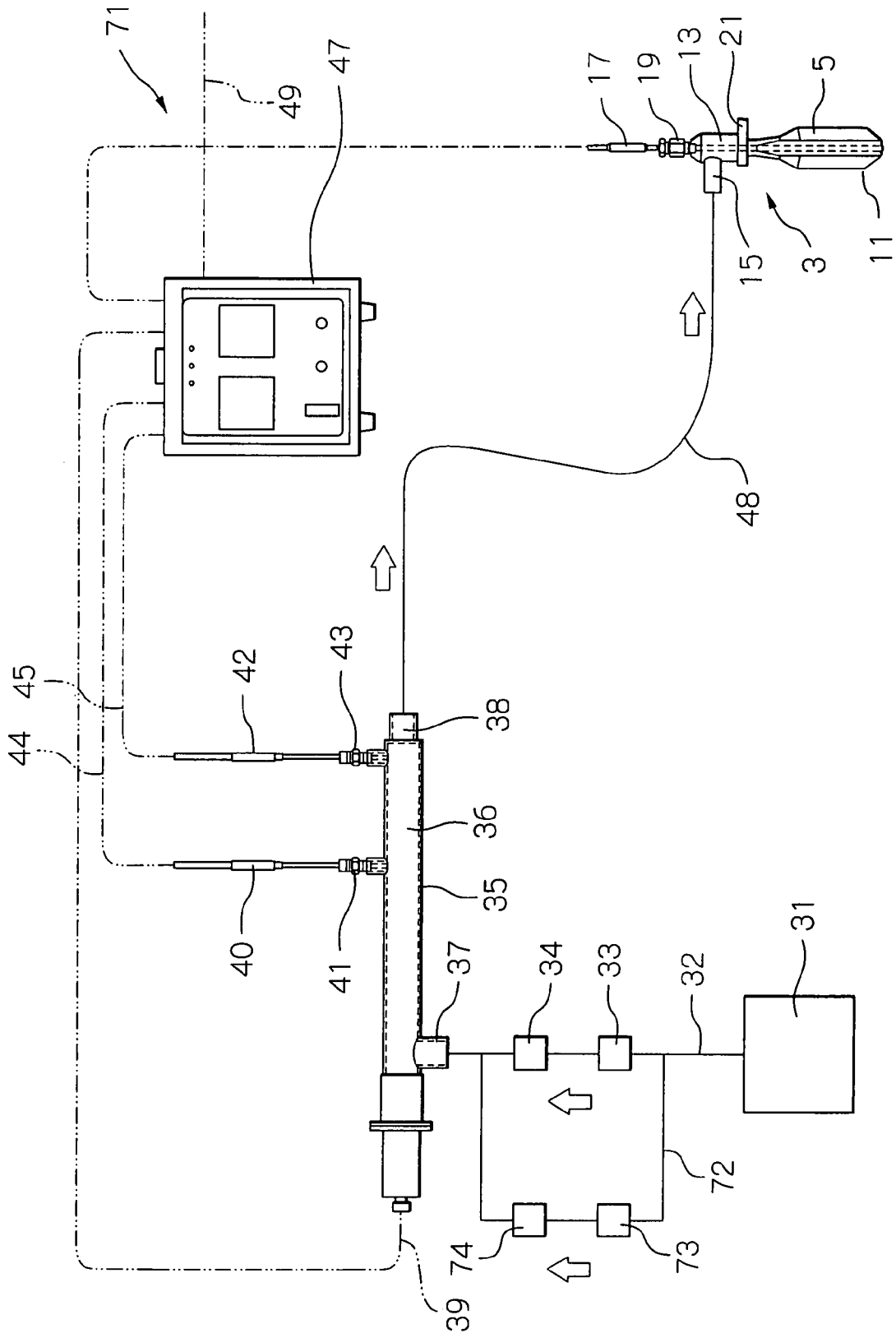
FIG. 7 is a circuit diagram showing the arrangement of a steam-replacement deaeration apparatus according to a third embodiment of the present invention.
Figure 8:
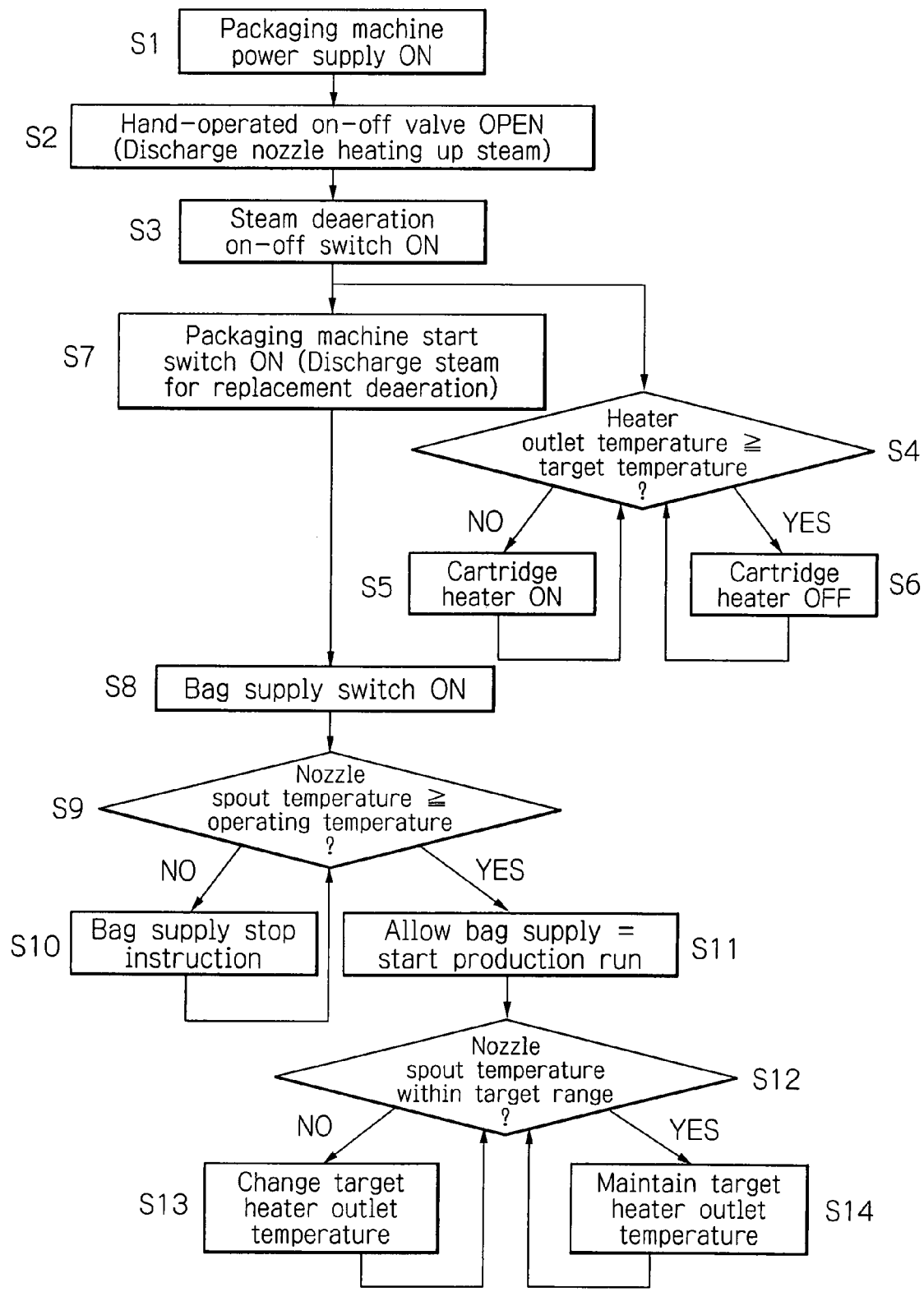
FIG. 8 is a flowchart showing the operation of the steam-replacement deaeration apparatus according to the third embodiment.

Next, a deaeration apparatus 71 according to a third embodiment of the present invention will be explained with reference to FIGS. 7 and 8. FIG. 7 is a circuit diagram showing the arrangement of the deaeration apparatus 71. FIG. 8 is a flowchart showing the operation of the deaeration apparatus 71. First, the arrangement of the deaeration apparatus 71 will be explained with reference to FIG. 7.

The greater part of the basic arrangements of the nozzle 3 and other constituent members used in the deaeration apparatus 71 and the circuit thereof is the same as that of the first embodiment. Therefore, the same constituent members are denoted by the same reference numerals as used in the first embodiment, and a description thereof is omitted herein. The deaeration apparatus 71 differs from the deaeration apparatus 1 of the first embodiment in that the deaeration apparatus 71 is provided with a heat-up steam supply passage 72 for heating up the nozzle 3. The heat-up steam supply passage 72 is provided between the steam supply source 31 and the heating device 35 in parallel to the primary steam supply passage 32. The heat-up steam supply passage 72 is provided with a pressure-reducing valve 73 and a hand-operated on-off valve 74. As will be described later, steam is continuously supplied to the nozzle 3 through the heat-up steam supply passage 72 before bag packaging is started. The bag packaging operation is maintained in standby mode until the temperature of steam injected from the nozzle 3 reaches a predetermined operating temperature.

Next, the operation of the deaeration apparatus 71 according to the third embodiment will be explained with reference to FIG. 8. First, at step S1, the power supply of the packaging machine A is turned on, and the temperature sensors 17, 40 and 42 turn on. Next, at step S2, the on-off valve 74 provided in the heat-up steam supply passage 72 is opened. Consequently, steam flows from the steam supply source 31 to the nozzle 3 through the heat-up steam supply passage 72, the heating device 35 and the secondary steam supply passage 48. At this time, heating up of steam is not performed because the heater 36 of the heating device 35 is off. Next, at step S3, the switch of the deaeration apparatus 71 is turned on, and thus the temperature control of the heating device 35 is started. That is, at step S4, the steam temperature at the outlet of the heating device 35 is detected by the sensor 42, and the detected steam temperature is compared with the target temperature of steam at the heater outlet, i.e. first target temperature. If the detected steam temperature has not yet reached the first target temperature, the heater 36 is turned on at step S5. If the detected steam temperature has already reached the first target temperature, the heater 36 is turned off at step S6. The temperature control of the heating device 35 is still continued thereafter. Steam flowing to the heating device 35 through the heat-up steam supply passage 72 is supplied to the nozzle 3 after being heated in the heating device 35.

When the packaging machine start switch is turned on at step S7, the entire packaging machine A enters an idling mode. That is, the turntable T starts intermittent rotation. The deaeration apparatus 71 opens and closes the automatic on-off valve 34 in the primary steam supply passage 32 at the same timing as in the case of performing an actual deaeration operation, thus starting the discharge of steam for steam-replacement deaeration. Consequently, from this point of time, the nozzle 3 injects both the above-described steam continuously supplied thereto through the heat-up steam supply passage 72 and steam intermittently supplied thereto through the primary steam supply passage 32. Thus, heated steam is supplied to the nozzle 3 prior to starting the packaging operation, thereby warming the nozzle 3 and the secondary steam supply passage 48 leading thereto so that the temperature of steam injected from the nozzle 3 reaches a predetermined operating temperature.

When the switch of the bag supply device S is turned on at step S8, the temperature of steam at the spout 11 of the nozzle 3 that is detected by the sensor 17 is compared with a predetermined operating temperature at step S9. If the detected steam temperature has not yet reached the operating temperature, the supply of bags is kept in the stopped state at step S10. If the detected steam temperature has already reached the operating temperature, the supply of bags is allowed at step S11. Thus, the supply of bags is started, and the packaging operation is commenced. More specifically, the bag supply device S starts to supply bags B, and as the turntable T rotates, various operations such as filling of an article to be packaged are performed at respective steps of the bag packaging process. The nozzle 3 of the deaeration apparatus 71 is inserted into each bag at a predetermined timing to inject steam thereinto. Thus, steam-replacement deaeration is performed. It should be noted that although the above-described operating temperature is set lower than the target temperature of steam at the nozzle spout, i.e. second target temperature, which will be described later, steam at the operating temperature provides a satisfactory replacement rate. Hence, products treated at this operating temperature are non-defective. At the subsequent step S12, the temperature of steam at the spout 11 of the nozzle 3 is compared with the target nozzle spout steam temperature, i.e. second target temperature. In this embodiment, unlike in the first and second embodiments, the second target temperature is set as a predetermined temperature range. If the measured temperature is within the target temperature range, the target temperature of steam at the heater outlet, i.e. first target temperature, is maintained as it is. If the measured temperature is not within the target temperature range, the first target temperature is changed and reset to control the system so that the steam temperature at the spout 11 of the nozzle 3 falls within the second target temperature range. These control operations are the same as in the first and second embodiments. Therefore, a detailed description thereof is omitted herein. It should be noted that the first target temperature can be set on the basis of the difference between the actual steam temperature and the median in the second target temperature range or the upper or lower limit value thereof. Although in the foregoing description the operating temperature is explained as a constant value, it may be set as a certain temperature range to perform control so that the supply of bags is stopped when the temperature of steam injected from the nozzle 3 becomes abnormally high in excess of the upper limit value of the operating temperature range owing to some trouble.

It should be noted that steam supplied through the heat-up steam supply passage 72 flows continuously, as has been stated above. In this regard, the steam supplied through the heat-up steam supply passage 72 is lower in discharge pressure or flow rate than steam supplied through the primary steam supply passage 32. The reason why steam is supplied through the heat-up steam supply passage 72 as a continuous flow of low flow rate is as follows. It is possible to perform the same control as in the normal deaeration operation in the idling mode before the start of production. That is, it is possible to intermittently supply steam at high pressure and high flow rate to heat up the nozzle 3 and so forth. In this case, however, it is difficult to rapidly heat up the nozzle 3 to the operating temperature because the injection of steam is performed intermittently and each injection is performed for a short period of time. Consequently, the standby time needed until the start of production is undesirably long. It is also possible to heat up the nozzle 3 and so forth by continuously supplying steam of the same pressure and flow rate as in the case of the deaeration operation. This heat-up method, however, will give rise to adverse effects in terms of safety and working environment because the discharge pressure or flow rate of steam is high. If automatic control is performed by using the second temperature sensor 17 provided at the spout 11 of the nozzle 3, the temperature at the nozzle 3 will rise rapidly because the discharge pressure or flow rate of steam is high. Even if the discharge of steam is stopped by using a signal from the second temperature sensor 17, the temperature of the nozzle 3 will overshoot and become higher than is necessary. Because an excessively high temperature of the nozzle 3 exerts an adverse effect on the replacement deaeration state, it is necessary to wait for the temperature of the nozzle 3 to lower from this level to an appropriate operating temperature, resulting in a long standby time needed until the start of operation. For these reasons, the present invention heats up the nozzle 3 by continuously supplying steam at an appropriate pressure or flow rate. It should be noted that at step S7 and steps following it the nozzle 3 is supplied with both steam continuously supplied through the heat-up steam supply passage 72 and steam intermittently supplied through the primary steam supply passage 32, as has been stated above. However, there is no possibility of the temperature of the nozzle 3 overshooting because the steam supply through the primary steam supply passage 32 is performed intermittently.

Further, in this embodiment, the on-off valve 74 provided in the heat-up steam supply passage 72 is a hand-operated valve. Therefore, the supply of steam through the heat-up steam supply passage 72 is continued even after the steam temperature at the spout 11 of the nozzle 3 has reached the operating temperature unless the on-off valve 74 is closed by a manual operation. This, however, does not exert an influence on the deaeration operation because the flow rate of steam supplied through the heat-up steam supply passage 72 is lower than the flow rate of steam discharged for deaeration.

Figure 9:
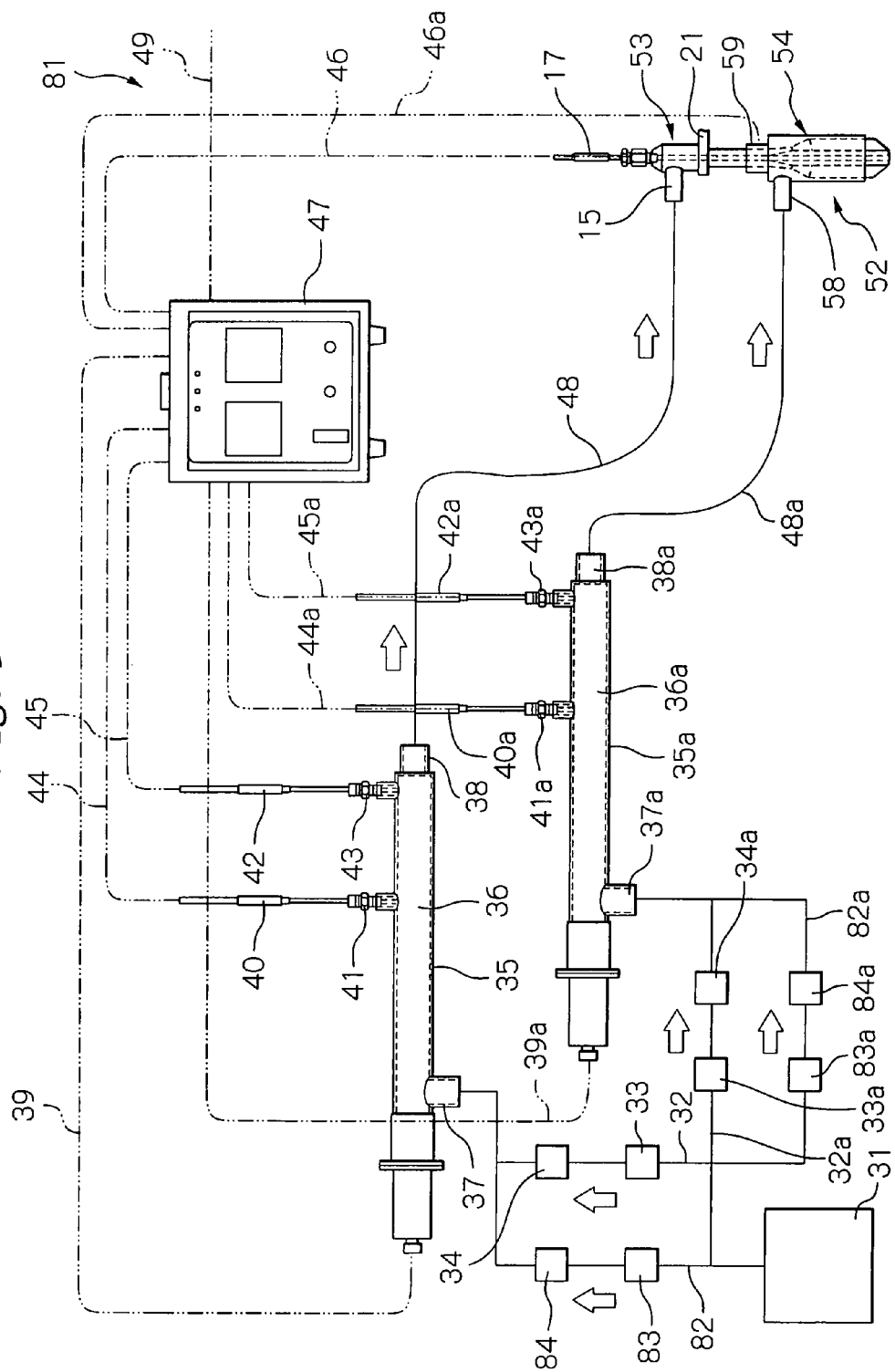
FIG. 9 is a circuit diagram showing the arrangement of a steam-replacement deaeration apparatus according to a fourth embodiment of the present invention.

Next, a deaeration apparatus 81 according to a fourth embodiment of the present invention will be explained with reference to FIGS. 9 and 10. FIG. 9 is a circuit diagram showing the arrangement of the deaeration apparatus 81. FIG. 10 is a flowchart showing the operation of the deaeration apparatus 81. First, the arrangement of the deaeration apparatus 81 will be explained with reference to FIG. 9.

The deaeration apparatus 81 is the same as the deaeration apparatus 51 of the second embodiment in the greater part of the basic arrangements of the constituent members used in the deaeration apparatus 81 and the circuit thereof, starting with the nozzle 52 of the double-tube type formed from the inner nozzle member 53 as a first nozzle member and the outer nozzle member 54 as a second nozzle member. Therefore, the same constituent members are denoted by the same reference numerals as used in the second embodiment, and a description thereof is omitted herein. The deaeration apparatus 81 differs from the deaeration apparatus 51 of the second embodiment in that heat-up steam supply passages 82 and 82a are provided in parallel to the primary steam supply passages 32 and 32a, respectively, as shown in the figure. The heat-up steam supply passages 82 and 82a are provided with respective pressure-reducing valves 83 and 83a and respective automatic on-off valves 84 and 84a. Before bag packaging is started, steam is continuously supplied to the inner and outer nozzle members 53 and 54 through the heat-up steam supply passages 82 and 82a, as will be described later. The bag packaging operation is maintained in standby mode until the temperature of steam injected from the nozzle members 53 and 54 reaches a predetermined operating temperature. The fourth embodiment differs from the third embodiment in that the on-off valves 84 and 84a provided in the heat-up steam supply passages 82 and 82a are automatic on-off valves.

Next, the operation of the deaeration apparatus 81 according to the fourth embodiment will be explained with reference to FIG. 10. First, at step S1, the power supply of the packaging machine A is turned on, and the temperature sensors 17, 59, 40, 40a, 42 and 42s turn on. Next, at step S2, the switch of the deaeration apparatus 81 is turned on. Consequently, the supply of steam from the steam supply source 31 to the heat-up steam supply passages 82 and 82a is controlled, and the temperature control of the heating devices 35 and 35a is started. That is, at step S3, steam temperatures at the spouts of the inner and outer nozzle members 53 and 54, which are detected by the second temperature sensors 17 and 59, are each compared with a predetermined operating temperature. If the detected steam temperatures are lower than the operating temperature, the automatic on-off valves 84 and 84a are opened at step S4. Consequently, steam heated in the heating devices 35 and 35a flows into the nozzle members 53 and 54 to heat them. When the target operating temperature has been reached, the automatic on-off valves 84 and 84a are closed at step S5 to stop the supply of steam to the heat-up steam supply passages 82 and 82a. It should be noted that if the operation at step S9 or S10 (described later) is not carried out immediately after step S5 and the nozzle spout temperatures have lowered below the operating temperature during waiting for the operation, the supply of steam is restarted at step S4. Meanwhile, at step S6, steam temperatures at the outlets of the heating devices 35 and 35a are detected by the sensors 42 and 42a and compared with a target temperature of steam at the heating device outlets, i.e. first target temperature. If the first target temperature has not yet been reached, the heaters 36 and 36a are turned on at step S7. If the first target temperature has already been reached, the heaters 36 and 36a are turned off at step S8. The temperature control of the heating devices 35 and 35a is continued still thereafter.

When the packaging machine start switch is turned on at step S9 following the turning on of the switch of the deaeration apparatus 81 at step S2, the entire packaging machine A enters an idling mode. That is, the turntable T starts intermittent rotation. The deaeration apparatus 81 opens and closes the automatic on-off valves 34 and 34a in the primary steam supply passages 32 and 32a at the same timing as in the case of performing an actual deaeration operation, thus starting the discharge of steam for steam-replacement deaeration. Consequently, from this point of time, the nozzle 52 injects both the above-described steam continuously supplied thereto through the heat-up steam supply passages 82 and 82a and steam intermittently supplied thereto through the primary steam supply passages 32 and 32a. When the predetermined operating temperature has been reached, the heat-up steam supply passages 82 and 82a are closed, as has been stated above.

When the switch of the bag supply device S is thereafter turned on at step S10, the temperatures of steam at the spouts of the nozzle members 53 and 54 that are detected by the sensors 17 and 59 are each compared with the predetermined operating temperature at step S11. If the detected steam temperatures have not yet reached the operating temperature, the supply of bags is kept in the stopped state at step S12. If the detected steam temperatures have already reached the operating temperature, the supply of bags is allowed at step S13. Thus, the supply of bags is started, and the packaging operation is commenced. Deaeration by the deaeration apparatus 81 is also started. At the subsequent step S14, the temperatures of steam at the spouts of the nozzle members 53 and 54 are compared with a target nozzle spout steam temperature, i.e. second target temperature. If the measured temperatures are within the target temperature range, the target temperature of steam at the heater outlets, i.e. first target temperature, is maintained as it is (step S16). If the measured temperatures are not within the target temperature range, the target temperature at the heater outlets, i.e. first target temperature, is changed and reset (step S15) to control the system so that the steam temperature at the spouts of the nozzle members 53 and 54 fall within the second target temperature range. The fourth embodiment is the same as the third embodiment in that the above-described operating temperature is set lower than the target temperature of steam at the spouts of the nozzle members 53 and 54, i.e. second target temperature, and the second target temperature is set as a predetermined temperature range.

In the fourth embodiment, once the steam temperature at each nozzle spout has reached the operating temperature, the automatic on-off valve is closed to stop the supply of steam through the heat-up steam supply passage. Therefore, the consumption of steam can be suppressed, and the running cost can be reduced.

Although in the fourth embodiment, heat-up steam supply passages are provided for both the inner and outer nozzle members 53 and 54, only either of the nozzle members 53 and 54 may be provided with a heat-up steam supply passage. In such a case, if the outer nozzle member 54 is provided with a heat-up steam supply passage, both the inner and outer nozzle members 53 and 54 can be heated up efficiently because the outer nozzle member 54 is heated from the inside thereof and the inner nozzle member 53 is heated from the outside thereof.

Although in the third embodiment the on-off valve in the heat-up steam supply passage is a hand-operated valve, it may be an automatic on-off valve and controlled as in the fourth embodiment. It is also possible to use hand-operated valves as the on-off valves provided in the heat-up steam supply passages in the fourth embodiment and to control them as in the third embodiment.

It should be noted that the present invention is not limited to the foregoing embodiments but can be modified in a variety of ways.

What is claimed is:

1. A steam-replacement deaeration apparatus for use in a bag packaging machine, said apparatus comprising:
    a nozzle comprising, proximate a distal end thereof, a spout to be inserted into a packaging bag;
    a steam supply source for supplying steam to said nozzle;
    a heating device that heats steam to be supplied to said nozzle;
    a primary steam supply passage connected at opposite ends thereof to said steam supply source and said heating device, respectively;
    a secondary steam supply passage connected at opposite ends thereof to said heating device and said nozzle, respectively;
    a first temperature sensor disposed near an outlet for steam of said heating device to measure a temperature of steam near said outlet;
    a second temperature sensor disposed in said nozzle to measure a temperature of steam near the spout of said nozzle; and
    means for controlling said heating device operatively connected to said first temperature sensor, said second temperature sensor and said heating device; said controlling means receives input of a first target temperature for steam at said first temperature sensor and input of a second target temperature for steam at said second temperature sensor, said controlling means resets said first target temperature on a basis of said second target temperature and a temperature measured by said second temperature sensor, and said controlling means controls said heating device on a basis of the first target temperature and a temperature measured by said first temperature sensor.

2. The steam-replacement deaeration apparatus of claim 1 in combination with a bag packaging machine, wherein said bag packaging machine comprises a bag supply device that supplies at least one bag, said means for controlling said heating device being adapted to control the start and stop of the supply of a bag performed by said bag supply device on a basis of a temperature detected by said second temperature sensor.

3. The steam-replacement deaeration apparatus of claim 2, further comprising:
    a heat-up steam supply passage for continuously supplying steam to said nozzle to heat said steam prior to the start of the supply of a bag performed by said bag supply device;
    wherein supply of steam through said heat-up steam supply passage is controlled by said means for controlling said heating device.

4. The steam-replacement deaeration apparatus of claim 3, wherein said heat-up steam supply passage is positioned between said steam supply source and said heating device in parallel to said primary steam supply passage.

5. The steam-replacement deaeration apparatus of claim 1, wherein said nozzle comprises a double-tube structure with an inner first nozzle member and an outer second nozzle member, said second temperature sensor comprising a sensor for each of the first nozzle member and the second nozzle member, said heating device comprising a first heating device and a second heating device respectively for said first nozzle member and said second nozzle member, said first temperature sensor comprising a sensor for each of said first heating device and second heating device, and said first nozzle member and said second nozzle member being connected to said steam supply source through said first heating device and said second heating device by respective primary and secondary steam supply passages.

6. The steam-replacement deaeration apparatus of claim 5 in combination with a bag packaging machine, wherein said bag packaging machine comprises a bag supply device that supplies at least one bag, said means for controlling said heating device being adapted to control the start and stop of the supply of the bag performed by said bag supply device on a basis of a temperature detected by at least one of the second temperature sensor provided for said first nozzle member or the second temperature sensor provided for said second nozzle member.

7. The steam-replacement deaeration apparatus of claim 6, wherein said means for controlling said heating device controls the start and stop of the supply of a bag on a basis of a temperature detected by the second temperature sensor provided for said second nozzle member.

8. The steam-replacement deaeration apparatus of claim 7, further comprising:
    a heat-up steam supply passage for continuously supplying steam to said nozzle to heat said steam prior to the start of the supply of a bag performed by said bag supply device, said heat-up steam supply passage being provided for at least said second nozzle member;
    wherein the supply of steam through said heat-up steam supply passage is controlled by said means for controlling said heating device.

9. The steam-replacement deaeration apparatus of claim 8, wherein said heat-up steam supply passages are positioned between said steam supply source and said respective heating devices in parallel to said respective primary steam supply passages.

10. A steam-replacement deaeration apparatus for use in a bag packaging machine, said apparatus comprising:
    a nozzle comprising, proximate a distal end thereof, a spout to be inserted into a packaging bag;
    a steam supply source for supplying steam to said nozzle;
    a heating device that heats steam to be supplied to said nozzle;
    a primary steam supply passage connected at opposite ends thereof to said steam supply source and said heating device, respectively;
    a secondary steam supply passage connected at opposite ends thereof to said heating device and said nozzle, respectively;
    a first temperature sensor disposed near an outlet for steam of said heating device to measure a temperature of steam near said outlet;
    a second temperature sensor disposed in said nozzle to measure a temperature of steam near the spout of said nozzle; and means for controlling said heating device operatively connected to said first temperature sensor, said second temperature sensor and said heating device; said controlling means receives input of a first target temperature for steam at said first temperature sensor and input of a second target temperature range for steam at said second temperature sensor, said controlling means resets said first target temperature on a basis of said second target temperature range and a temperature measured by said second temperature sensor, and said controlling means controls said heating device on a basis of the first target temperature and a temperature measured by said first temperature sensor.

11. The steam-replacement deaeration apparatus of claim 10 in combination with a bag packaging machine, wherein said bag packaging machine comprises a bag supply device that supplies at least one bag, said means for controlling said heating device being adapted to control the start and stop of the supply of a bag performed by said bag supply device on a basis of a temperature detected by said second temperature sensor.

12. The steam-replacement deaeration apparatus of claim 11, further comprising:
a heat-up steam supply passage for continuously supplying steam to said nozzle to heat said steam prior to the start of the supply of a bag performed by said bag supply device;
wherein supply of steam through said heat-up steam supply passage is controlled by said means for controlling said heating device.

13. The steam-replacement deaeration apparatus of claim 12, wherein said heat-up steam supply passage is positioned between said steam supply source and said heating device in parallel to said primary steam supply passage.

14. The steam-replacement deaeration apparatus of claim 10, wherein said nozzle comprises a double-tube structure with an inner first nozzle member and an outer second nozzle member, said second temperature sensor comprising a sensor for each of the first nozzle member and the second nozzle member, said heating device comprising a first heating device and a second heating device respectively for said first nozzle member and said second nozzle member, said first temperature sensor comprising a sensor for each of said first heating device and second heating device, and said first nozzle member and said second nozzle member being connected to said steam supply source through said first heating device and said second heating device by respective primary and secondary steam supply passages.

15. The steam-replacement deaeration apparatus of claim 14 in combination with a bag packaging machine, wherein said bag packaging machine comprises a bag supply device that supplies at least one bag, said means for controlling said heating device being adapted to control the start and stop of the supply of the bag performed by said bag supply device on a basis of a temperature detected by at least one of the second temperature sensor provided for said first nozzle member or the second temperature sensor provided for said second nozzle member.

16. The steam-replacement deaeration apparatus of claim 15, wherein said means for controlling said heating device controls the start and stop of the supply of a bag on a basis of a temperature detected by the second temperature sensor provided for said second nozzle member.

17. The steam-replacement deaeration apparatus of claim 16, further comprising:
a heat-up steam supply passage for continuously supplying steam to said nozzle to heat said steam prior to the start of the supply of a bag performed by said bag supply device, said heat-up steam supply passage being provided for at least said second nozzle member;
wherein the supply of steam through said heat-up steam supply passage is controlled by said means for controlling said heating device.

18. The steam-replacement deaeration apparatus of claim 17, wherein said heat-up steam supply passages are positioned between said steam supply source and said respective heating devices in parallel to said respective primary steam supply passages.

19. A steam-replacement deaeration apparatus for use in a bag packaging machine, said apparatus comprising:
a nozzle comprising, proximate a distal end thereof, a spout to be inserted into a packaging bag;
a steam supply source for supplying steam to said nozzle;
a heating device that heats steam to be supplied to said nozzle;
a primary steam supply passage connected at opposite ends thereof to said steam supply source and said heating device, respectively;
a secondary steam supply passage connected at opposite ends thereof to said heating device and said nozzle, respectively;
a first temperature sensor disposed near an outlet for steam of said heating device to measure a temperature of steam near said outlet;
a second temperature sensor disposed in said nozzle to measure a temperature of steam near the spout of said nozzle; and
a controller which receives input of a first target temperature for steam at said first temperature sensor and input of a second target temperature for steam at said second temperature sensor, said controller changes and resets said first target temperature on a basis of said second target temperature and a temperature measured by said second temperature sensor, and said controller controls said heating device on a basis of the first target temperature and a temperature measured by said first temperature sensor.

20. The steam-replacement deaeration apparatus of claim 19 in combination with a bag packaging machine, wherein said bag packaging machine comprises a bag supply device that supplies at least one bag, said controller being adapted to control the start and stop of the supply of a bag performed by said bag supply device on a basis of a temperature detected by said second temperature sensor.

21. The steam-replacement deaeration apparatus of claim 20, further comprising:
a heat-up steam supply passage for continuously supplying steam to said nozzle to heat said steam prior to the start of the supply of a bag performed by said bag supply device;
wherein supply of steam through said heat-up steam supply passage is controlled by said controller.

22. The steam-replacement deaeration apparatus of claim 21, wherein said heat-up steam supply passage is positioned between said steam supply source and said heating device in parallel to said primary steam supply passage.

23. The steam-replacement deaeration apparatus of claim 19, wherein said nozzle comprises a double-tube structure with an inner first nozzle member and an outer second nozzle member, said second temperature sensor comprising a sensor for each of the first nozzle member and the second nozzle member, said heating device comprising a first heating device and a second heating device respectively for said first nozzle member and said second nozzle member, said first temperature sensor comprising a sensor for each of said first heating device and second heating device, and said first nozzle member and said second nozzle member being connected to said steam supply source through said first heating device and said second heating device by respective primary and secondary steam supply passages.

24. The steam-replacement deaeration apparatus of claim 23 in combination with a bag packaging machine, wherein said bag packaging machine comprises a bag supply device that supplies at least one bag, said controller being adapted to control the start and stop of the supply of the bag performed by said bag supply device on a basis of a temperature detected by at least one of the second temperature sensor provided for said first nozzle member or the second temperature sensor provided for said second nozzle member.

25. The steam-replacement deaeration apparatus of claim 24, wherein said controller controls the start and stop of the supply of a bag on a basis of a temperature detected by the second temperature sensor provided for said second nozzle member.

26. The steam-replacement deaeration apparatus of claim 25, further comprising:
a heat-up steam supply passage for continuously supplying steam to said nozzle to heat said steam prior to the start of the supply of a bag performed by said bag supply device, said heat-up steam supply passage being provided for at least said second nozzle member;
wherein the supply of steam through said heat-up steam supply passage is controlled by said controller.

27. The steam-replacement deaeration apparatus of claim 26, wherein said heat-up steam supply passages are positioned between said steam supply source and said respective heating devices in parallel to said respective primary steam supply passages.

28. A steam-replacement deaeration apparatus for use in a bag packaging machine, said apparatus comprising:
a nozzle comprising, proximate a distal end thereof, a spout to be inserted into a packaging bag;
a steam supply source for supplying steam to said nozzle;
a heating device that heats steam to be supplied to said nozzle;
a primary steam supply passage connected at opposite ends thereof to said steam supply source and said heating device, respectively;
a secondary steam supply passage connected at opposite ends thereof to said heating device and said nozzle, respectively;
a first temperature sensor disposed near an outlet for steam of said heating device to measure a temperature of steam near said outlet;
a second temperature sensor disposed in said nozzle to measure a temperature of steam near the spout of said nozzle; and
a controller which receives input of a first target temperature for steam at said first temperature sensor and input of a second target temperature range for steam at said second temperature sensor, said controller changes and resets said first target temperature on a basis of said second target temperature range and a temperature measured by said second temperature sensor, and said controller controls said heating device on a basis of the first target temperature and a temperature measured by said first temperature sensor.

29. The steam-replacement deaeration apparatus of claim 28 in combination with a bag packaging machine, wherein said bag packaging machine comprises a bag supply device that supplies at least one bag, said controller being adapted to control the start and stop of the supply of a bag performed by said bag supply device on a basis of a temperature detected by said second temperature sensor.

30. The steam-replacement deaeration apparatus of claim 29, further comprising:
a heat-up steam supply passage for continuously supplying steam to said nozzle to heat said steam prior to the start of the supply of a bag performed by said bag supply device;
wherein supply of steam through said heat-up steam supply passage is controlled by said controller.

31. The steam-replacement deaeration apparatus of claim 30, wherein said heat-up steam supply passage is positioned between said steam supply source and said heating device in parallel to said primary steam supply passage.

32. The steam-replacement deaeration apparatus of claim 28, wherein said nozzle comprises a double-tube structure with an inner first nozzle member and an outer second nozzle member, said second temperature sensor comprising a sensor for each of the first nozzle member and the second nozzle member, said heating device comprising a first heating device and a second heating device respectively for said first nozzle member and said second nozzle member, said first temperature sensor comprising a sensor for each of said first heating device and second heating device, and said first nozzle member and said second nozzle member being connected to said steam supply source through said first heating device and said second heating device by respective primary and secondary steam supply passages.

33. The steam-replacement deaeration apparatus of claim 32 in combination with a bag packaging machine, wherein said bag packaging machine comprises a bag supply device that supplies at least one bag, said controller being adapted to control the start and stop of the supply of the bag performed by said bag supply device on a basis of a temperature detected by at least one of the second temperature sensor provided for said first nozzle member or the second temperature sensor provided for said second nozzle member.

34. The steam-replacement deaeration apparatus of claim 33, wherein said controller controls the start and stop of the supply of a bag on a basis of a temperature detected by the second temperature sensor provided for said second nozzle member.

35. The steam-replacement deaeration apparatus of claim 34, further comprising:
a heat-up steam supply passage for continuously supplying steam to said nozzle to heat said steam prior to the start of the supply of a bag performed by said bag supply device, said heat-up steam supply passage being provided for at least said second nozzle member;
wherein the supply of steam through said heat-up steam supply passage is controlled by said controller.

36. The steam-replacement deaeration apparatus of claim 35, wherein said heat-up steam supply passages are positioned between said steam supply source and said respective heating devices in parallel to said respective primary steam supply passages.

* * * * *